United States Patent
Pepper

(12) 
(10) Patent No.: US 6,183,477 B1
(45) Date of Patent: Feb. 6, 2001

(54) ATTACHMENT TOOL FOR DRILL GUIDE

(75) Inventor: John R. Pepper, Germantown, TN (US)

(73) Assignee: Smith & Nephew, Inc., Memphis, TN (US)

( * ) Notice: Under 35 U.S.C. 154(b), the term of this patent shall be extended for 0 days.

(21) Appl. No.: 09/148,688

(22) Filed: Sep. 4, 1998

(51) Int. Cl.$^7$ .................................................. A61B 17/58
(52) U.S. Cl. ........................................................... 606/104
(58) Field of Search .............................. 606/62, 64, 96, 606/104

(56) References Cited

U.S. PATENT DOCUMENTS

| | | | |
|---|---|---|---|
| 4,103,683 | * | 8/1978 | Neufeld ................................. 606/64 |
| 4,465,065 | | 8/1984 | Gotfried . |
| 4,622,959 | | 11/1986 | Marcus . |
| 4,733,654 | | 3/1988 | Marino . |
| 4,862,883 | | 9/1989 | Freeland . |
| 4,911,153 | | 3/1990 | Border . |
| 4,913,137 | * | 4/1990 | Azer et al. ............................. 606/64 |
| 5,047,034 | | 9/1991 | Sohngen . |
| 5,176,681 | | 1/1993 | Lawes et al. . |
| 5,178,621 | | 1/1993 | Cook et al. . |
| 5,295,991 | | 3/1994 | Frigg . |
| 5,334,192 | | 8/1994 | Behrens . |
| 5,346,496 | | 9/1994 | Pennig . |
| 5,352,228 | | 10/1994 | Kummer et al. . |
| 5,429,641 | | 7/1995 | Gotfried . |
| 5,458,600 | | 10/1995 | Stapert et al. . |
| 5,478,341 | | 12/1995 | Cook et al. . |
| 5,713,902 | | 2/1998 | Friedl . |
| 5,728,128 | | 3/1998 | Crickenberger et al. . |
| 5,741,266 | * | 4/1998 | Moran et al. ........................... 606/96 |

OTHER PUBLICATIONS

Synthes; The Titanium Unreamed Femoral Nail System; published in the Original Instruments and Implants of the Association for the Study of Internal Fixation—AO/ASIF.

* cited by examiner

*Primary Examiner*—Gene Mancene
*Assistant Examiner*—Eduardo C. Robert
(74) *Attorney, Agent, or Firm*—Fulbright & Jaworski L.L.P.

(57) ABSTRACT

An attachment tool for attaching a drill guide to a medical implant such as an intramedullary nail including a first end and a housing. The first end includes a first opening that allows a fastener to pass through and thread into the implant thus attaching the tool. The housing includes a second opening whose longitudinal axis is preferably offset from the longitudinal axis of the first opening. The housing also includes a guide surface with a grove for directing a driving tool to the second opening. The driving tool is inserted through the second opening to drive the fastener. The driving tool can be inserted and removed during the procedure. In one embodiment, the fastener is cannulated to afford a surgeon access to the interior of the implant. The housing also includes a plurality of holes that can be used as drill guide holes or to attach separate drill guides or other orthopedic devices.

37 Claims, 5 Drawing Sheets

ATTACHMENT TOOL FOR DRILL GUIDE

BACKGROUND OF THE INVENTION

1. Field of the Invention

The present invention relates to drill guides and other medical instruments that are attached to medical implants such as intramedullary nails which assist in the performance of surgical steps such as targeting and guiding the installation of bone screws from outside the body. More particularly, the invention is directed to a tool that facilitates the detachment of drill guides and the like from medical implants and minimizes the time to perform the detachment step and the size of the incision through body tissue in the vicinity of the implant.

2. Description of the Prior Art

During a procedure to insert an intramedullary nail, a drill guide is connected to the intramedullary nail with a connecting bolt. The connecting bolt is threaded into the proximal end of the intramedullary nail aligned generally with the longitudinal axis of the intramedullary nail. During insertion of the intramedullary nail into the patient, a mallet is used to strike an insertion driver which communicates the impact through the drill guide to the intramedullary nail. After insertion of the intramedullary nail, the drill guide provides alignment for drilling transverse bores through the bone to accommodate transverse screws to lock the intramedullary nail to the bone. In addition, other orthopedic devices that require precise alignment or sturdy connection to the intramedullary nail, such as drills, modular drill guides, reaming devices, guide tubes, guide pins, fasteners, or removal drivers, can be attached to the drill guide.

The connection of the drill guide to the intramedullary nail is an important part of the femoral shaft fracture procedure. The connecting bolt is often obscured by soft tissue and cannot be seen by the surgeon. Getting a tool to the connecting bolt can be difficult, may require several minutes, and often results in soft tissue damage. In addition, a large incision is often required to accommodate the required tool. An example of such a drill guide showing a conventional attachment is disclosed in U.S. Pat. No. 4,911,153.

One prior art device, the Synthes drill guide, allows remote actuation of the connecting bolt. However, the Synthes device achieves remote actuation through a long, bent neck for guiding a universal-jointed driving tool to the bolt. The neck is permanently attached and continuously interferes with soft tissue during the medical procedure. In addition, the bolt used with the Synthes device is not cannulated. Cannulation of the bolt is desirable to allow the surgeon access to the interior of an implant.

It is an object of the present invention to provide an attachment tool for an implant drill guide that can be remotely actuated with minimal soft tissue damage. It is a further object of the present invention to provide an attachment tool that is capable of using cannulated fasteners. These objects are solved by the attachment tool of the present invention.

SUMMARY OF THE INVENTION

The problems discussed above have been solved by providing an attachment tool for use with a medical implant such as an intramedullary nail which includes a housing having a first end adapted for connection to a medical implant. The first end includes a first opening through which passes an elongated threaded fastener such as a bolt or screw that is designed to be inserted into an elongated opening in the implant. The housing includes a guide surface and may include a second opening that intersects and is offset from the first opening for guiding a driving tool into contact with the fastener at an angle offset from the axis of the fastener. The housing is designed to minimize the size of the necessary incision in the body tissue while facilitating connection of drill guides and other orthopedic devices. The housing may have various shapes depending upon the shape of the implant, drill guide or other orthopedic device to which it connects. In the case of a drill guide for an intramedullary nail, the housing is preferably U-shaped, L-shaped, or S-shaped.

The first end includes a tab or other type of alignment and positioning member for engaging a slot or the like formed in the proximal end of an implant such as an intramedullary nail. When the tab is aligned with the slot, the first opening is aligned with the opening in the intramedullary nail so that the threaded fastener can easily be inserted in the nail opening through the first opening. Tab and slot alignment also assures that holes drilled using the integral drill guide holes or an attached drill guide align with implant fastening holes.

The fastener is preferably a bolt with a female hexagonally-shaped driving head. The driving tool, on the other hand, has a driving head that is adapted to engage and drive the fastener from a angle offset relative to the axis of the fastener. One example of such a driving head is a rounded male hexagonally-shaped driving head that is designed to cooperate with the hexagonally-shaped female driving head on the fastener.

The guide surface for the driving tool can include a groove for receiving the driving tool and guiding it to an opening in the housing. Said opening could be the first opening, but is preferably a second opening that intersects the first opening at a point where the driving tool can extend through the second opening and engage the fastener for driving it into place. If the fastener is cannulated, i.e., has an opening along its axis, a guide rod can be inserted through the fastener to help reduce the fracture during surgery.

The tool can include one or more drill guide hole(s) in the guide housing aligned with openings in the implant when the guide housing is connected to the implant for targeting a drill to form openings in the tissue and bone around the implant to receive implant fastening screws. The drill guide holes could alternatively be formed in an attachment for the tool instead of being formed in the tool itself.

A tool of the type generally described can be used to guide and align a driving tool to a fastener more quickly and with less damage to tissue surrounding an implant than in prior art devices. Moreover, with a cannulated fastener, the tool allows a guide rod to be inserted for fracture reduction.

BRIEF DESCRIPTION OF THE DRAWINGS

The invention will be understood by those skilled in the art when a detailed description of the preferred embodiment set forth below is considered in conjunction with the appended drawings, in which.

DETAILED DESCRIPTION OF THE PREFERRED EMBODIMENT

Figure 1:
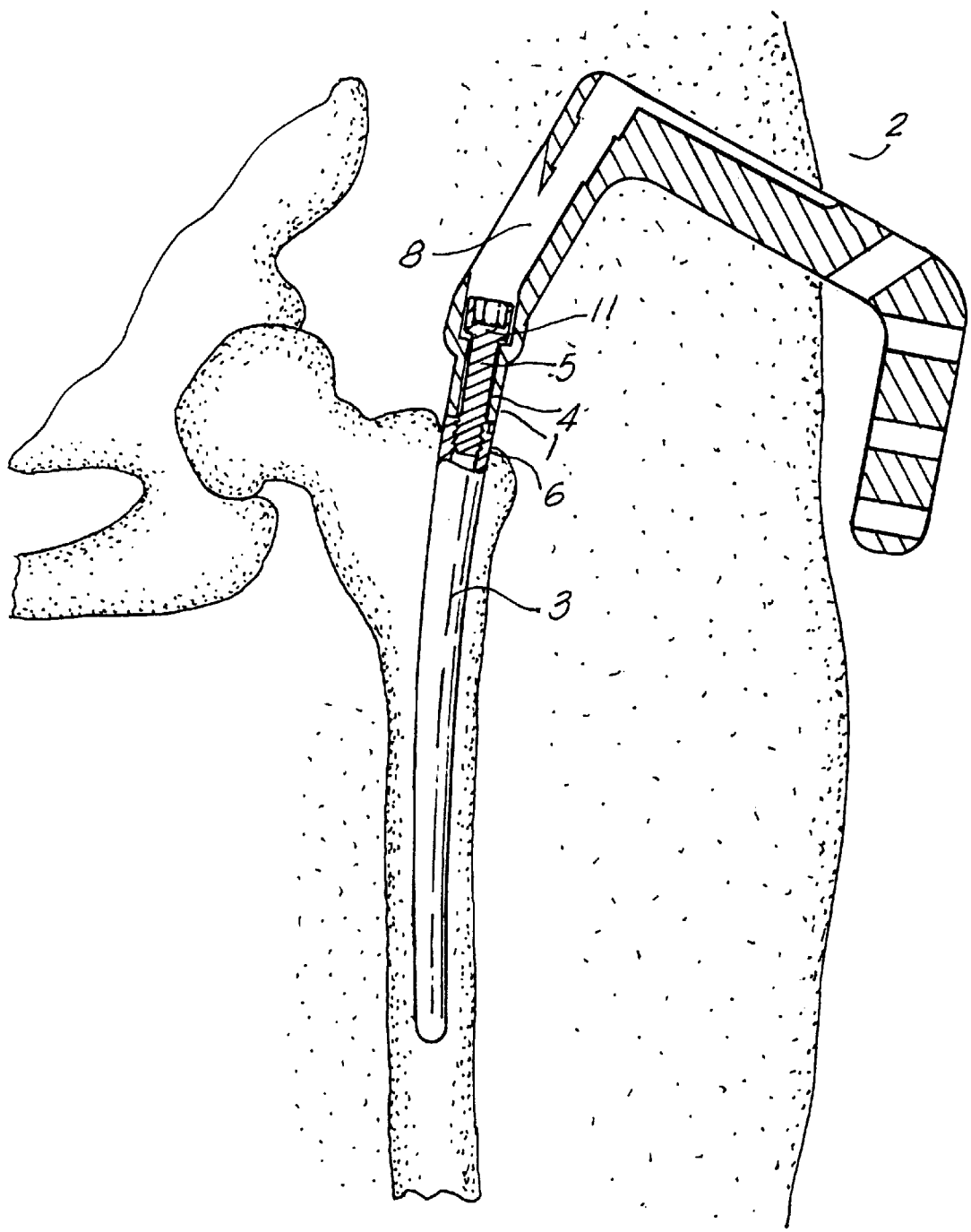
FIG. 1 is a general view showing the attachment tool of the present invention attached to an intramedullary nail in a femur in a human body.
Figure 2:
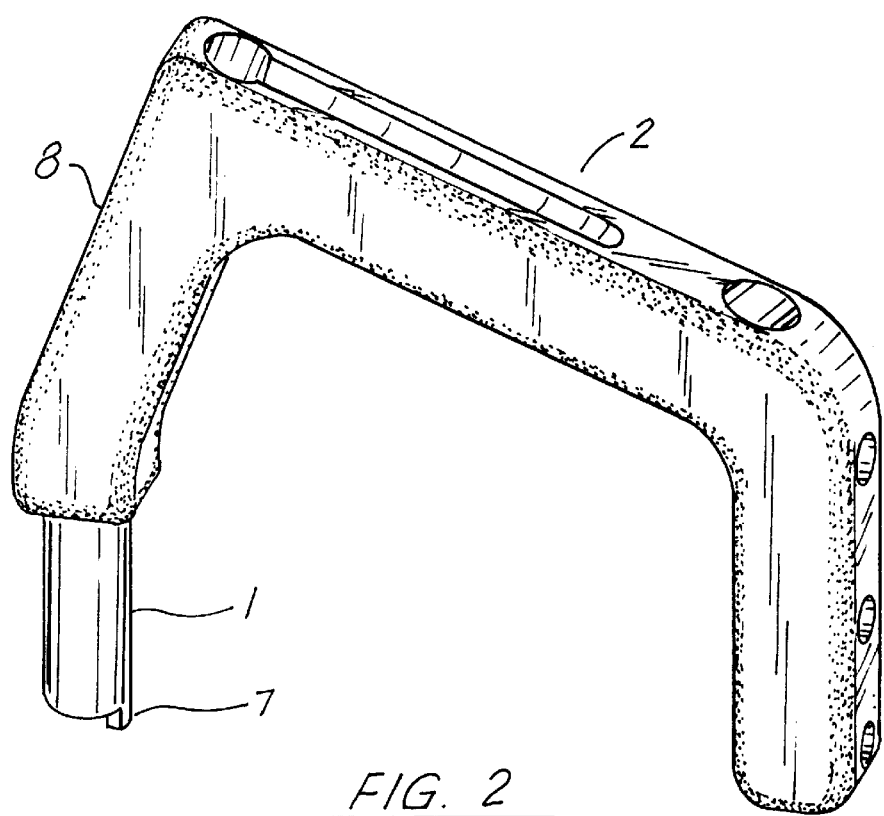
FIG. 2 is a perspective view of the attachment tool of the present invention.
Figure 3:
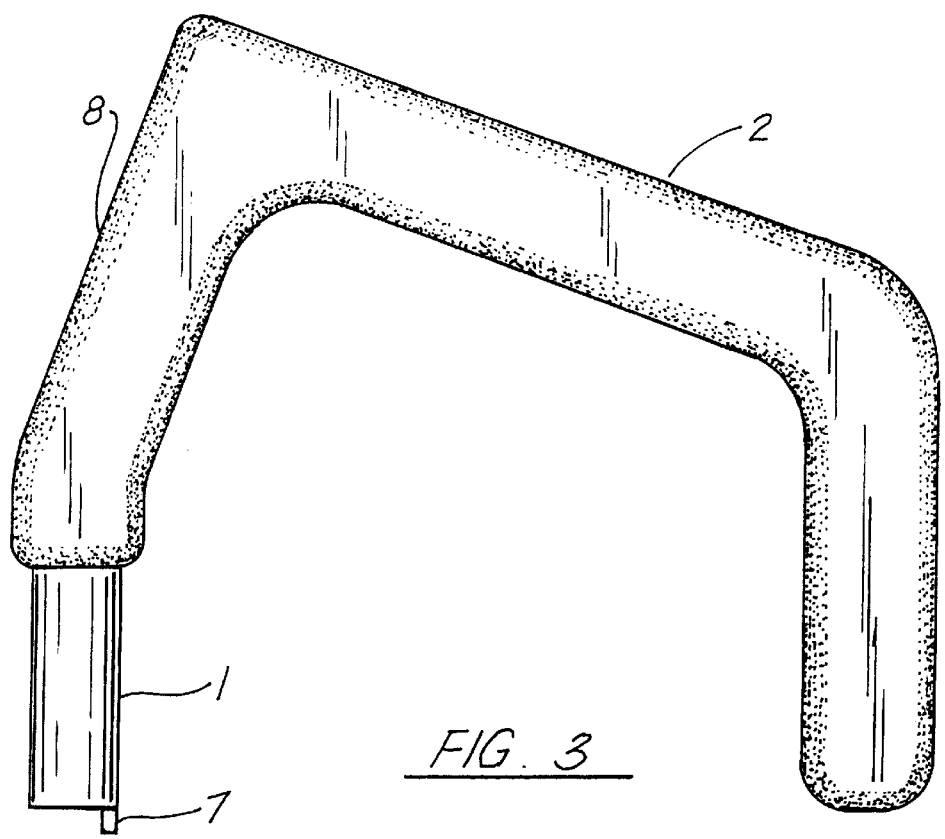
FIG. 3 is a side view of the attachment tool of the present invention.
Figure 4:
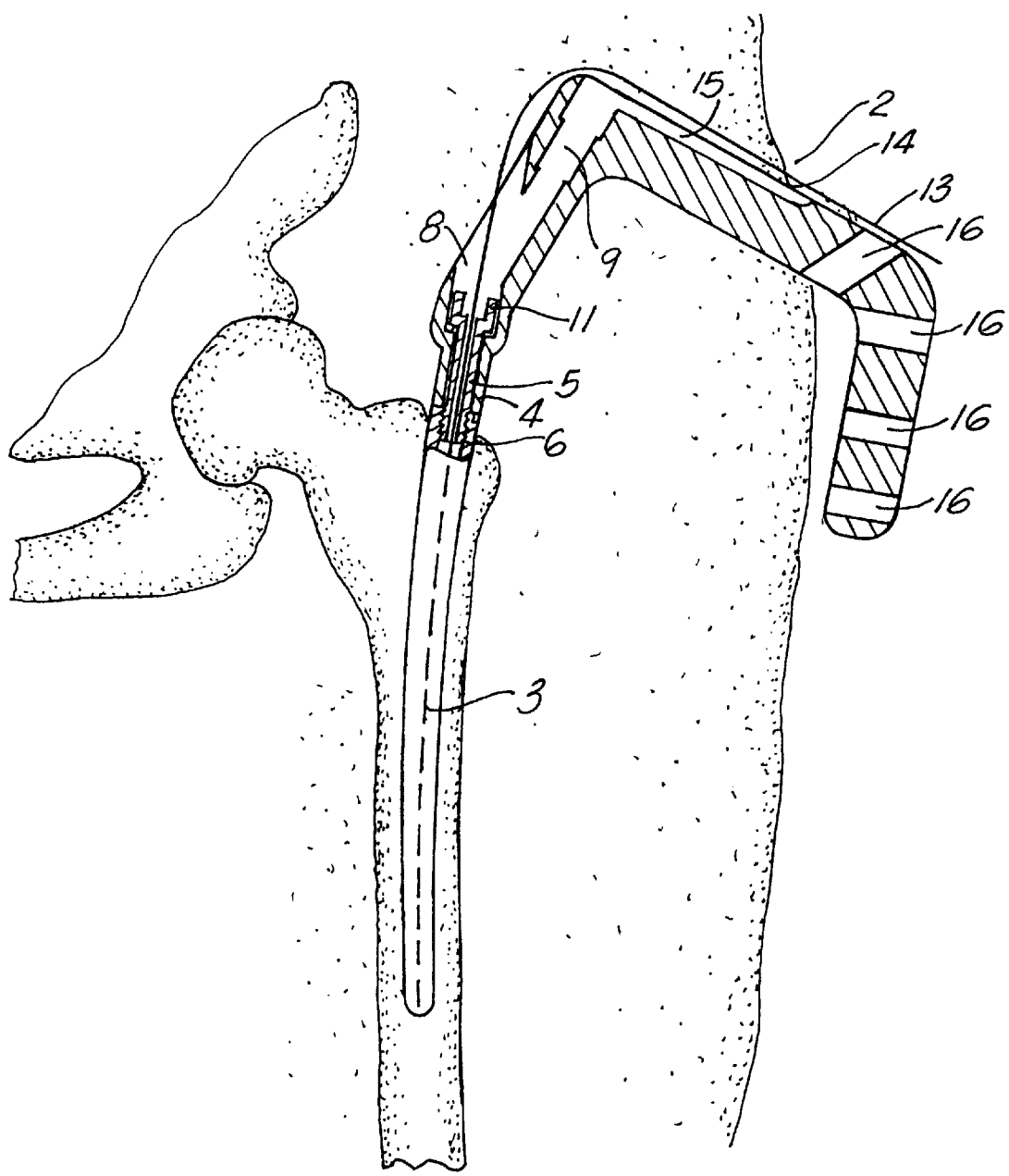
FIG. 4 is a sectional view of the attachment tool of the present invention attached to an intramedullary nail in a femur in a human body further showing a guide rod inserted through the attachment tool through a cannulated bolt and into the interior of the intramedullary nail.

Referring now to FIGS. 1 through 3, the attachment tool of the present invention is shown. The preferred embodiment of the attachment tool includes a housing 2 with a first end 1. The first end 1 is cylindrical and designed to engage the proximal end of an implant such as an intramedullary nail 3. A first opening 4 extends through the first end 1 and is sized to allow the threads and shaft of a fastener 5 to pass through and engage threads 6 on the interior of the proximal end of the intramedullary nail 3. The first end 1 includes a tab that engages a matching slot (not shown) on the proximal end of the intramedullary nail 3 to prevent relative rotation.

The housing 2 of the attachment tool extends from the first end 1. The housing 2 may be a separate piece that is fixedly attached to the first end 1 to form the attachment tool. In the preferred embodiment, the first end 1 and housing 2 are a unitary machined or cast piece. The housing 2 includes a fastener hole 8 whose longitudinal axis is aligned with the longitudinal axis of the first opening 4 in the first end 1. The fastener hole 8 is sized large enough to allow the head 11 of the fastener 5 to pass through and rotate.

Referring now to FIGS. 4 through 7, the housing 2 further includes a guide surface 14 for directing a driving tool 10 to an opening and into operational contact with the fastener 5 when the attachment tool is inserted percutaneously into a patient and the opening is obscured by soft tissue. The guide surface 14 includes longitudinal geometric features such as ridges or depressions to direct the driving tool 10. In the preferred embodiment, the guide surface 14 includes a semi-circular groove 15 to facilitate insertion of the driving tool 10. The groove 15 is oriented at approximately 90 degrees relative to a central axis of the first opening 4. The guide surface 14 may direct the driving tool 10 to the first opening 4. In the preferred embodiment, the guide surface 14 directs the driving tool 10 to a second opening 9 whose longitudinal axis is offset from the longitudinal axis of the fastener hole 8 and first opening 4. The offset angle of the second opening 9 allows the surgeon greater clearance in executing surgical procedures. The optimum offset angle for the second opening 9 varies depending upon the application, although the maximum angle is limited by the need for the driving tool 10 to operationally engage the fastener 5 at the intersection of the longitudinal axis of the second opening 9 and the longitudinal axis of the fastener hole 8 and first opening 4.

Figure 5:
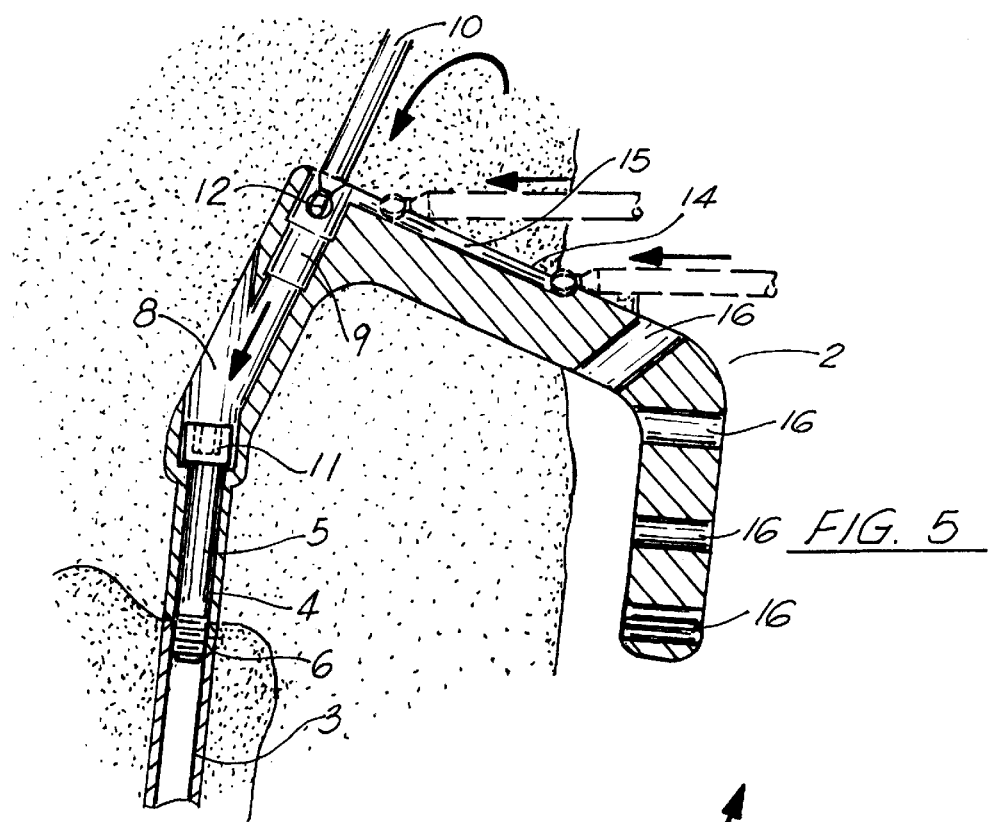
FIG. 5 is a sectional view of the attachment tool of the present invention attached to an intramedullary nail in a femur in a human body further showing the sequence for bringing the driving tool into contact with the fastener.
Figure 6:
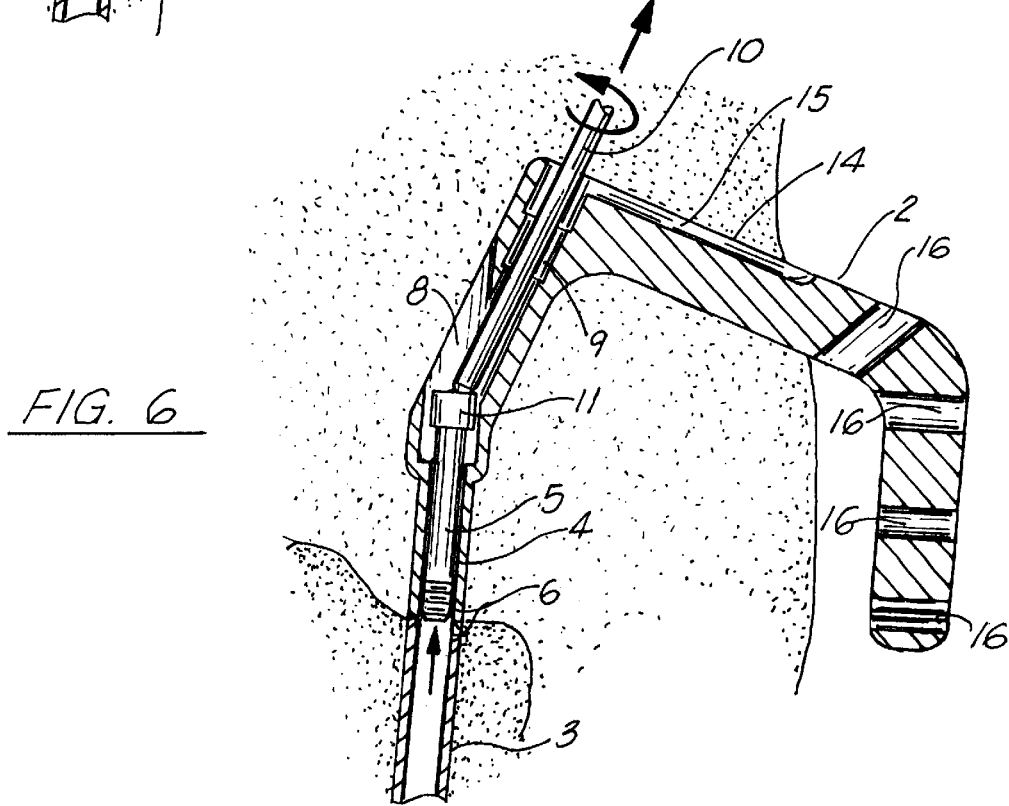
FIG. 6 is a sectional view of the attachment tool of the present invention attached to an intramedullary nail in a femur in a human body further showing the fastener being detached from the intramedullary nail through use of the driving tool.
Figure 7:
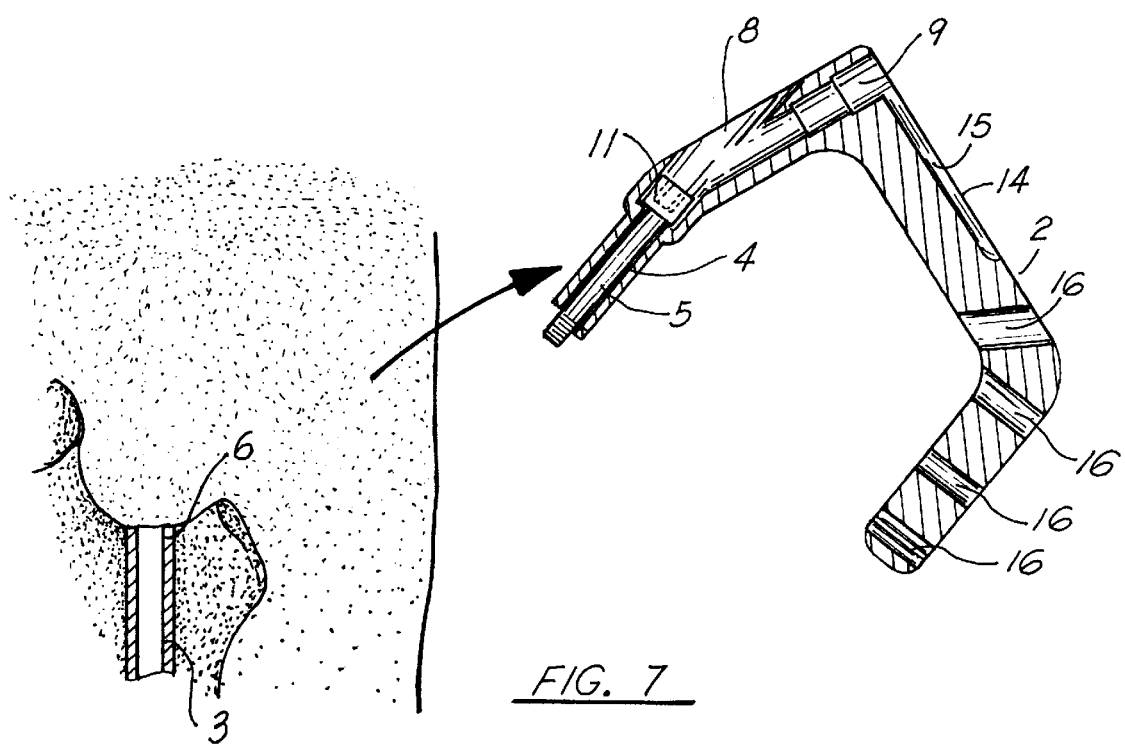
FIG. 7 is a sectional view of the attachment tool of the present invention attached being removed with the fastener from an intramedullary nail in a femur in a human body.

The fastener 5 passes through the fastener hole 8 and the fastener's shaft and threads pass through the first opening 4 to engage matching threads 6 on the interior of the intramedullary nail 3. The head 11 of the fastener 5 may have any of a number of geometric shapes that can be driven by a tool, including hexagonal head, Phillips head, slotted head, torx head, Allen head, or various other configurations. In the preferred embodiment, the driving tool 10 is capable of driving the fastener 5 through the offset angle of the second opening 9. To accomplish this, the driving tool must have a flexible shaft, a U-joint, or some other offset driving mechanism. In the preferred embodiment, the driving tool has a one-piece rigid shaft with a driving end 12 shaped to operatively engage the head 11 of the fastener 5 at the second opening offset angle while still being able to be inserted and withdrawn from the attachment tool by the surgeon during the procedure. In the most preferred embodiment, the head 11 of the fastener 5 has an Allen head and the driving end 12 of the driving tool 10 is a ball end hex driver. Also as shown in FIG. 5, in the preferred embodiment, the fastener 5 is cannulated to allow the insertion of a guide rod 13 for fracture reduction and to otherwise afford the surgeon access to the interior of the implant 3.

In the preferred embodiment, the housing 2 has a high U-shaped arch to minimize the size of the necessary incision and to minimize soft tissue damage. Depending upon the geometry of the device to be attached to the attachment tool, the housing may also be L-shaped, S-shaped, or have any number of other shapes. The housing 2 also includes a plurality of holes 16 that can be used as drill guides or to attach further orthopedic devices such as drills, modular drill guides, reaming devices, guide tubes, guide pins, fasteners, insertion drivers, or removal drivers to the attachment tool.

From the preceding description of the preferred embodiment, it is evident that the objects of the invention are attained. Although the invention has been described and illustrated in detail, it is to be clearly understood that the same is intended to be taken by way of illustration and example only and is not to be taken by way of limitation. The spirit and scope of the invention are to be limited only by the terms of the appended claims.

I claim:

1. An attachment tool for use with a medical implant, comprising
   a) a housing having a first end adapted for connection to a medical implant;
   b) the first end having a first opening through which an elongated threaded fastener with a central axis can be inserted into the implant; and
   c) a guide surface on an exterior of the housing, said guide surface leading to the first opening and capable of guiding a driving tool into contact with the fastener.

2. The tool of claim 1, wherein the housing is shaped to minimize an incision site required for insertion and removal of the tool through body tissue.

3. The tool of claim 1, wherein the housing is shaped to be connected to a variety of external orthopedic devices selected from a group consisting of drills, modular drill guides, reaming devices, guide tubes, guide pins, fasteners, insertion drivers and removal drivers.

4. The tool claim 3, wherein the housing is generally U-shaped.

5. The tool of claim 1, wherein the first end includes an alignment device for engaging a matching alignment device in the proximal end of the implant.

6. The tool of claim 5, wherein the alignment device in the first end consists of a tab for engaging a slot in the proximal end of the implant.

7. The tool of claim 1, wherein the first opening includes an axis for alignment with an elongated central axis of the implant.

8. The tool of claim 1, wherein the guide surface includes a groove for receiving the driving tool and guiding the driving tool to the first opening.

9. The tool of claim 8, wherein the groove is oriented at approximately 90 degrees relative to a central axis of the first opening, and the groove is generally U-shaped in cross section so the driving tool can move along the groove at an angle relative to the axis of the first opening.

10. The tool of claim 1, and further including at least one drill guide hole in the housing for alignment with an opening in the implant when the housing is connected to the implant.

11. The tool of claim 1, and further including a drill guide adapted to be connected to the housing, said drill guide including at least one drill guide hole for alignment with an opening in the implant when the housing is connected to the implant.

12. An attachment tool for use with a medical implant, comprising:
 a) a housing having a first end adapted for connection to a medical implant;
 b) the first end having a first opening through which an elongated threaded fastener with a central axis can be inserted into the implant; and
 c) a second opening on a guide surface on the housing, said second opening intersecting and offset from the first opening for guiding a driving tool into contact with the fastener at an angle offset from the axis of the fastener.

13. The tool of claim 12, wherein the housing is shaped to minimize an incision site required for insertion and removal of the tool through body tissue.

14. The tool of claim 12, wherein the housing is shaped to be connected to a variety of external orthopedic devices selected from a group consisting of drills, modular drill guides, reaming devices, guide tubes, guide pins, fasteners, insertion divers and removal divers.

15. The tool of claim 12, wherein the housing is generally U-shaped.

16. The tool of claim 12, wherein the first end includes an alignment device for engaging a matching alignment device in a proximal end of the implant.

17. The tool of claim 16, wherein the alignment device in the first end consists of a tab for alignment with the proximal end of the implant.

18. The tool of claim 12, wherein the first opening includes an axis for alignment with an elongated central axis of the implant.

19. The tool of claim 12, wherein the guide surface includes a groove for receiving the driving tool and guiding the driving tool to the second opening.

20. The tool of claim 12, wherein the groove is oriented at approximately 90 degrees relative to a central axis of the second opening, and the groove is generally U-shaped in cross section so the driving tool can move along the groove at an angle relative to the axis of the second opening.

21. The tool of claim 12, and further including at least one drill guide hole in the housing for alignment with an opening in the implant when the housing is connected to the implant.

22. The tool of claim 12, and further including a drill guide adapted to be connected to the housing, said drill guide including at least one drill guide hole for alignment with an opening in the implant when the housing is connected to the implant.

23. A method for driving a threaded fastener for a medical implant comprising the steps of:
 a) aligning an attachment tool with an end of a medical implant, the tool having a first opening through which an elongated threaded fastener with a central axis can be inserted aligned with an elongated threaded opening in the implant;
 b) inserting the fastener into the opening in the implant through the first opening in the tool;
 c) connecting a driving tool to the fastener by moving the driving tool along a guide surface on an exterior of the tool and into the first opening; and
 d) rotating the driving tool to drive the fastener.

24. A method for driving a threaded fastener for a medical implant comprising the steps of:
 a) aligning an attachment tool with an end of a medical implant, the tool having a first opening through which an elongated threaded fastener with a central axis can be inserted aligned with an elongated threaded opening in the implant;
 b) inserting the fastener into the opening in the implant through the first opening in the tool;
 c) connecting a driving tool to the fastener at an angle offset from the axis of the fastener by moving the driving tool along a guide surface in the tool into a second opening in the tool which intersects and is offset from the first opening; and
 d) rotating the driving tool to drive the fastener.

25. An attachment tool for use with a medical implant, comprising:
 a) a first end adapted for connection to a medical implant;
 b) the first end having a first opening with a central axis through which an elongated threaded fastener can be inserted into the implant; and
 c) a guide surface extending from an exterior of the housing and leading to the first opening, wherein said guide surface has a central axis that intersects the central axis of the first opening, and said guide surface is capable of guiding a driving tool into contact with the fastener.

26. An intramedullary nail system comprising an intramedullary nail attached to a tool by a fastener, whereby said tool comprises:
 a) a first end adapted for connection to a medical implant;
 b) the first end having a first opening with a central axis through which an elongated threaded fastener can be inserted into the implant; and
 c) a guide surface extending from an exterior of the housing and leading to the first opening, wherein said guide surface is capable of guiding a driving tool into contact with the fastener.

27. The intramedullary nail system of claim 26, wherein the guide surface is capable of guiding a driving tool from a position outside a patient's body onto driving contact with the fastener when the intramedullary nail is positioned within an intramedullary canal of the patient.

28. The intramedullary nail system of claim 26, wherein the guide surface has a central axis that intersects the central axis of the first opening.

29. The tool of claim 26, wherein the fastener includes a bolt for connecting the housing to the implant.

30. The tool of claim 29, wherein the bolt is cannulated.

31. The tool of claim 26, wherein the fastener includes a bolt for connecting the housing to the implant and the driving tool is capable of driving the fastener through the offset of the second opening.

32. The tool of claim 31, wherein the bolt is cannulated.

33. The tool of claim 31, wherein the bolt includes a driving head having a recessed center portion.

34. The tool of claim 33, wherein the portion of the driving tool adapted to engage the recessed center portion of the driving head of the bolt is a rounded driving head.

35. A medical implant system comprising:
   a) a medical implant;
   b) an attachment tool having a first end adapted for connection to the medical implant;
   c) the first end having a first opening with a central axis through which an elongated threaded fastener can be inserted into the implant; and
   d) a guide surface extending from an exterior of the housing and leading to the first opening, wherein said guide surface has a central axis that intersects the central axis of the first opening, and said guide surface is capable of guiding a driving tool into contact with the fastener.

36. The medical implant system of claim 35, wherein the attachment tool further includes a second opening on the guide surface, said second opening intersecting and offset from the first opening for guiding the driving tool into contact with the fastener at an angle offset from the axis of the fastener.

37. The medical implant system of claim 35, wherein the guide surface is capable of guiding the driving tool from a position outside a patient's body onto driving contact with the fastener when the medical implant is positioned within an intramedullary canal of the patient.

* * * * *